(12) United States Patent
Martin et al.

(10) Patent No.: US 8,030,505 B2
(45) Date of Patent: Oct. 4, 2011

(54) BIODIESEL PRODUCTION METHOD

(75) Inventors: Abbey Martin, Clio, MI (US); Joseph E. Flynn, Saginaw, MI (US); Harold Lange, Sanford, MI (US)

(73) Assignee: B&P Process Equipment and Systems, LLC, Saginaw, MI (US)

( * ) Notice: Subject to any disclaimer, the term of this patent is extended or adjusted under 35 U.S.C. 154(b) by 788 days.

(21) Appl. No.: 11/962,619

(22) Filed: Dec. 21, 2007

(65) Prior Publication Data

US 2009/0163731 A1    Jun. 25, 2009

(51) Int. Cl.
*C11C 3/10*    (2006.01)
(52) U.S. Cl. ........................................ 554/168; 554/167
(58) Field of Classification Search .................. 554/167, 554/168
See application file for complete search history.

(56) References Cited

U.S. PATENT DOCUMENTS 5,354,878 A    10/1994    Connemann et al.

*Primary Examiner* — Deborah D Carr
(74) *Attorney, Agent, or Firm* — Reising Ethington P.C.

(57) ABSTRACT

A process for producing lower alkyl esters of higher fatty acids from an oil phase and lower alcohols, in a catalytic transesterification process in the presence of an alkaline catalyst. A reaction mixture is provided by mixing oil-phase fatty acids with a solution comprising methanol and an alkaline catalyst comprising sodium methylate. The transesterification reaction of the reaction mixture is accelerated by subjecting the reaction mixture to a temperature above the boiling point of methanol and pressurizing the reaction mixture sufficiently to prevent boil-off. A centrifugal separator separates glycerin phase from biodiesel phase of a resulting reaction product stream. The biodiesel phase is washed by counter-current extraction.

53 Claims, 3 Drawing Sheets

BIODIESEL PRODUCTION METHOD

CROSS-REFERENCES TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

This invention relates generally to a biodiesel production method for producing and washing biodiesel fuel.

2. Description of the Related Art Including Information Disclosed Under 37 CFR 1.97 and 1.98

It is known for a biodiesel fuel, i.e., lower alkyl esters of higher fatty acids, to be produced from an oil phase and lower alcohols in a catalytic transesterification process in the presence of an alkaline catalyst. For example, U.S. Pat. No. 5,354,878 issued 11 Oct. 1994 to Connemann et al. discloses a two-stage process for producing biodiesel as well as a process for washing biodiesel produced by the two-stage process. In a first transesterification and glycerin separation stage the Connemann et al. disclose mixing raw oil comprising oil-phase fatty acids, with a solution of methanol (MEOH) and an alkaline catalyst comprising sodium methylate at 150% stoichiometric MEOH. The resulting first stage reaction mixture is pumped into a first reactor. A glycerin phase is separated from the resulting first stage reaction product stream by passing the first stage reaction product through a first centrifugal separator. The glycerin phase of the first stage reaction product leaves the centrifugal separator in one stream and a biodiesel phase of the first stage reaction product is discharged in a second stream.

In the second stage, the above steps are repeated by mixing a non-recycled portion of the biodiesel phase of the first stage reaction product stream with additional alkaline catalyst. The resulting second stage reaction mixture is passed into a second reactor. Glycerin is separated from the resulting second stage reaction product stream by passing it through a second centrifugal separator. A resulting biodiesel phase of the second stage reaction product is passed (at a reaction state of 99.2 to 99.6% complete) to a stripping stage.

In the stripping stage, surplus unreacted methanol is stripped from the biodiesel phase of the second stage reaction product. The unreacted methanol is stripped by passing the biodiesel phase of the second stage reaction product through a vacuum distillation tower. The resulting evaporated methanol passes through a condensation system to be condensed and passed back to be recycled for use in the first stage of the Connemann et al. process. The stripped biodiesel phase of the second stage reaction product is passed to the next process stage.

From the stripping stage the stripped biodiesel phase of the second stage reaction product (or unwashed biodiesel product) passes through a first water wash step in which catalyst residue, water, soap, and remaining glycerin are washed from the unwashed biodiesel product by passing the unwashed biodiesel product along with water through a third centrifugal separator and operating the centrifugal separator to separate catalyst, soap, and glycerin from the unwashed biodiesel product. The resulting washed biodiesel product may optionally be passed through a second water wash step in which the washed biodiesel product is passed, with water, through a fourth centrifugal separator to remove additional NaOH, glycerin, and soap, resulting in a final biodiesel product having a purity of 99.2-99.6%.

The Connemann et al. patent therefore discloses a slow, unpressurized, low-temperature process that includes the use of reactor columns and at least two glycerin extraction points and a recycle circuit that recycles a portion of the biodiesel phase of the reaction product of each transesterification stage. More specifically, the Connemann et al. patent discloses the use of a pump mixer to both mix and propel the reaction mixture into the top of a reactor tank column, and beginning the transesterification reaction by passing the reaction mixture downward through the reactor tank column at a flow rate limited to a rate lower than a sinking rate of the glycerin separated from the reaction mixture. The downward flow of the reaction mixture through the reactor tank column must be slower than the glycerin sinking rate to allow sufficient time for transesterification. Consequently, to drive the reaction and remove sufficient glycerin, the Connemann et al. process includes the additional steps, in each transesterification stage, of pumping reaction mixture into a glycerin settling tank before reaching the centrifugal separator and then recycling a portion of the biodiesel phase of the reaction product stream through the glycerin settling tank. Both the reaction mixture and the recycled portion of the biodiesel phase of the reaction product stream experience a settling tank residence period of from 2 minutes to 2 hours (preferably 1 hour). Because a portion of the biodiesel phase of the reaction product stream is continuously recycled, only a portion of the biodiesel phase of each stage's reaction product stream is forwarded to subsequent stages in the process.

It's also known in the art to use a POD counterflow centrifugal separator in counter-current extraction processes. The POD is manufactured by and available from B&P Process Systems of Saginaw Mich. and includes a first inlet for receiving a first liquid into a radially outer region of a centrifuge tank of the POD. The centrifuge tank is rotatably supported on a centrifuge axis. The POD also includes a second inlet for receiving a second liquid into a central axial region of the centrifuge tank, the second liquid having a specific gravity greater than that of the first liquid. In a counter-current extraction process the centrifuge tank of the POD is spun about the centrifuge axis such that the second liquid is forced radially outward from the central axial region through the reaction mixture and through a series of concentric perforated cylindrical panels supported coaxially within the centrifuge tank in the path of the second liquid. This forces the second liquid to pass through the perforations in the panels, presenting additional surface area contact between the first and second liquids to allow one or more components of the second liquid to dissolve into or otherwise react with the first liquid. The POD further includes a first outlet that discharges the first liquid less the reacted or dissolved component and a second outlet that discharges the second liquid plus the reacted or dissolved component from the first liquid.

It would be desirable if biodiesel could be produced more quickly and using less equipment but without sacrificing purity.

BRIEF SUMMARY OF THE DISCLOSURE

A process for producing lower alkyl esters of higher fatty acids from an oil phase and lower alcohols, in a catalytic transesterification process in the presence of an alkaline catalyst is provided. The process including the steps of providing a reaction mixture by mixing oil comprising oil-phase fatty acids, with a solution comprising methanol (MEOH) and an alkaline catalyst comprising sodium methylate; and accelerating the transesterification reaction of the reaction mixture by subjecting the reaction mixture to a temperature above the boiling point of methanol and pressurizing the reaction mixture sufficiently to prevent boil-off.

Alternatively, the process may include providing a first stage reaction mixture by mixing oil comprising oil-phase fatty acids, with a solution comprising methanol (MEOH) and an alkaline catalyst comprising sodium methylate; and separating a first stage glycerin phase from a first stage biodiesel phase of a resulting first stage reaction product stream by passing the first stage reaction mixture through a first stage centrifugal separator comprising a series of perforated concentric panels separating an axial region from a rim region of the separator, such that the first stage glycerin and biodiesel phases pass through arrays of perforations in the panels of the series of concentric panels as the glycerin passes to the rim region and the first stage biodiesel phase passes to the axial region of the separator.

As a further alternative, the process may include providing a reaction mixture by mixing oil comprising oil-phase fatty acids, with a solution comprising methanol (MEOH) and an alkaline catalyst comprising sodium methylate; separating a glycerin phase from a biodiesel phase of a resulting reaction product stream; and washing the biodiesel phase using counter-current extraction. This allows high purity biodiesel to be produced more quickly, using less equipment, and requiring less floor space.

BRIEF DESCRIPTION OF THE SEVERAL VIEWS OF THE DRAWINGS

These and other features and advantages will become apparent to those skilled in the art in connection with the following detailed description and drawings of one or more embodiments of the invention, in which.

DETAILED DESCRIPTION OF INVENTION EMBODIMENT(S)

Figure 1A:
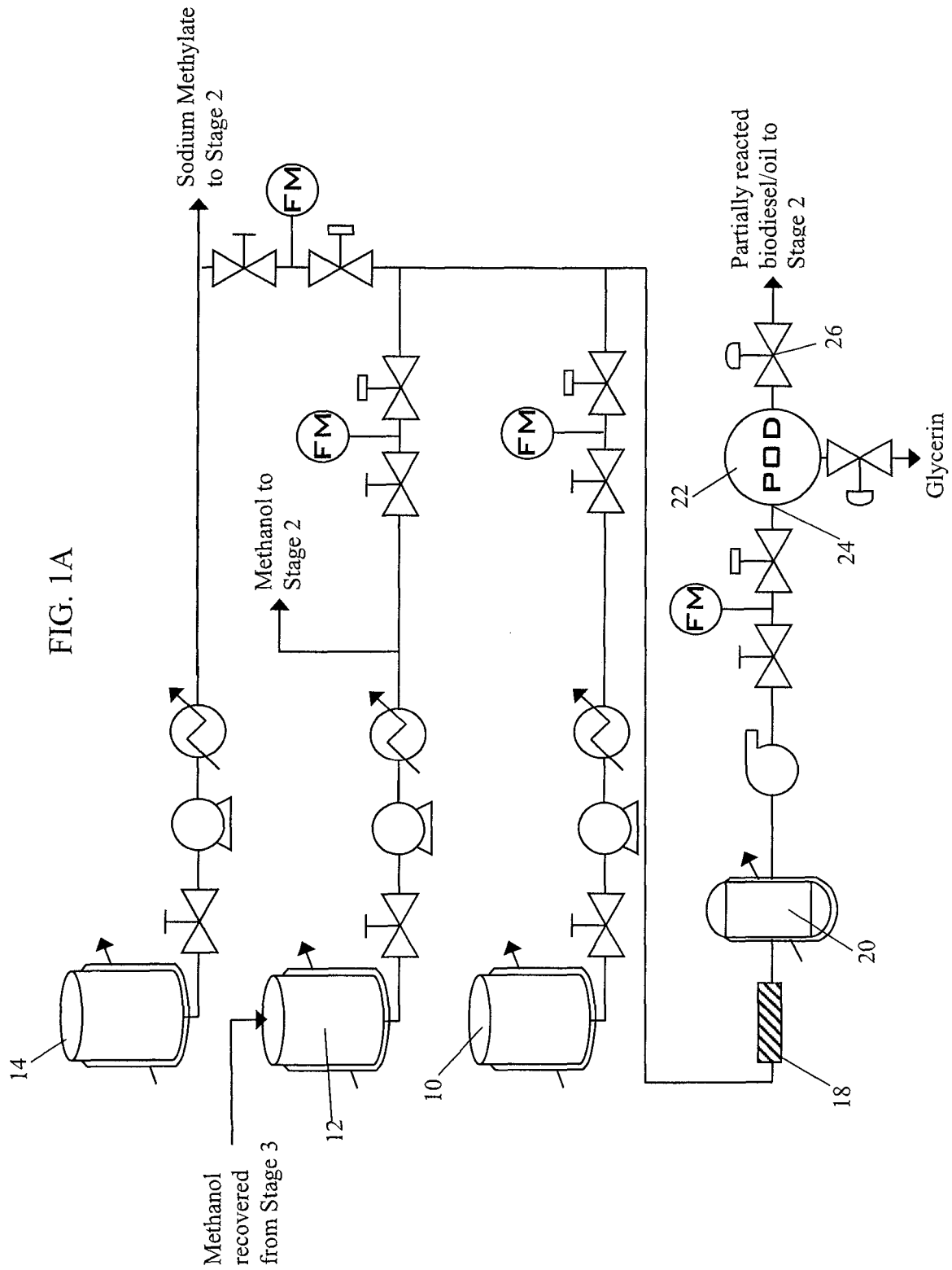
FIG. 1A is a process flow diagram showing a first transesterification stage of a biodiesel production process arranged according to the invention.
Figure 1B:
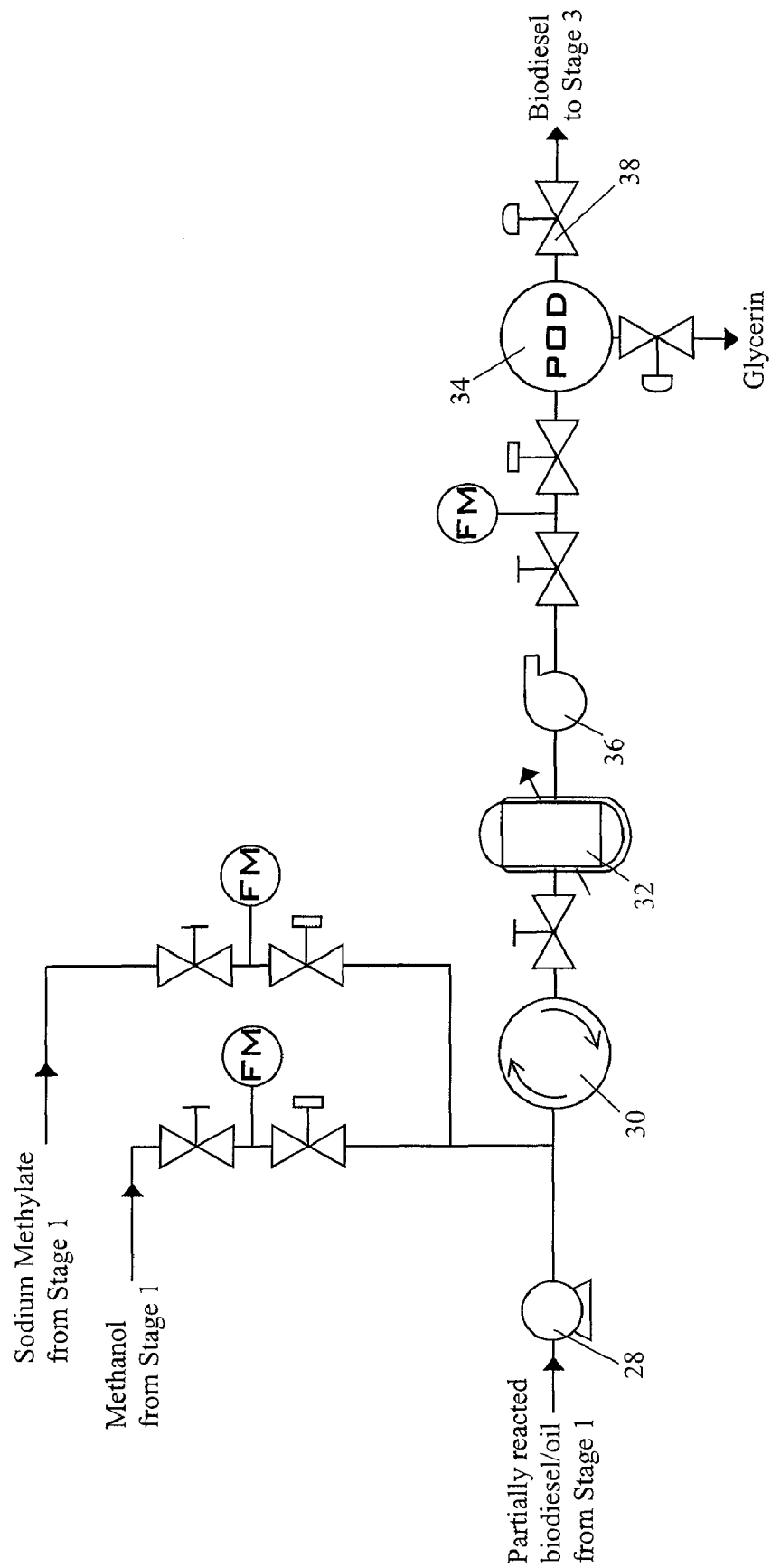
FIG. 1B is a process flow diagram showing a second transesterification stage of the biodiesel production process of FIG. 1A and continuing from FIG. 1A.
Figure 1C:
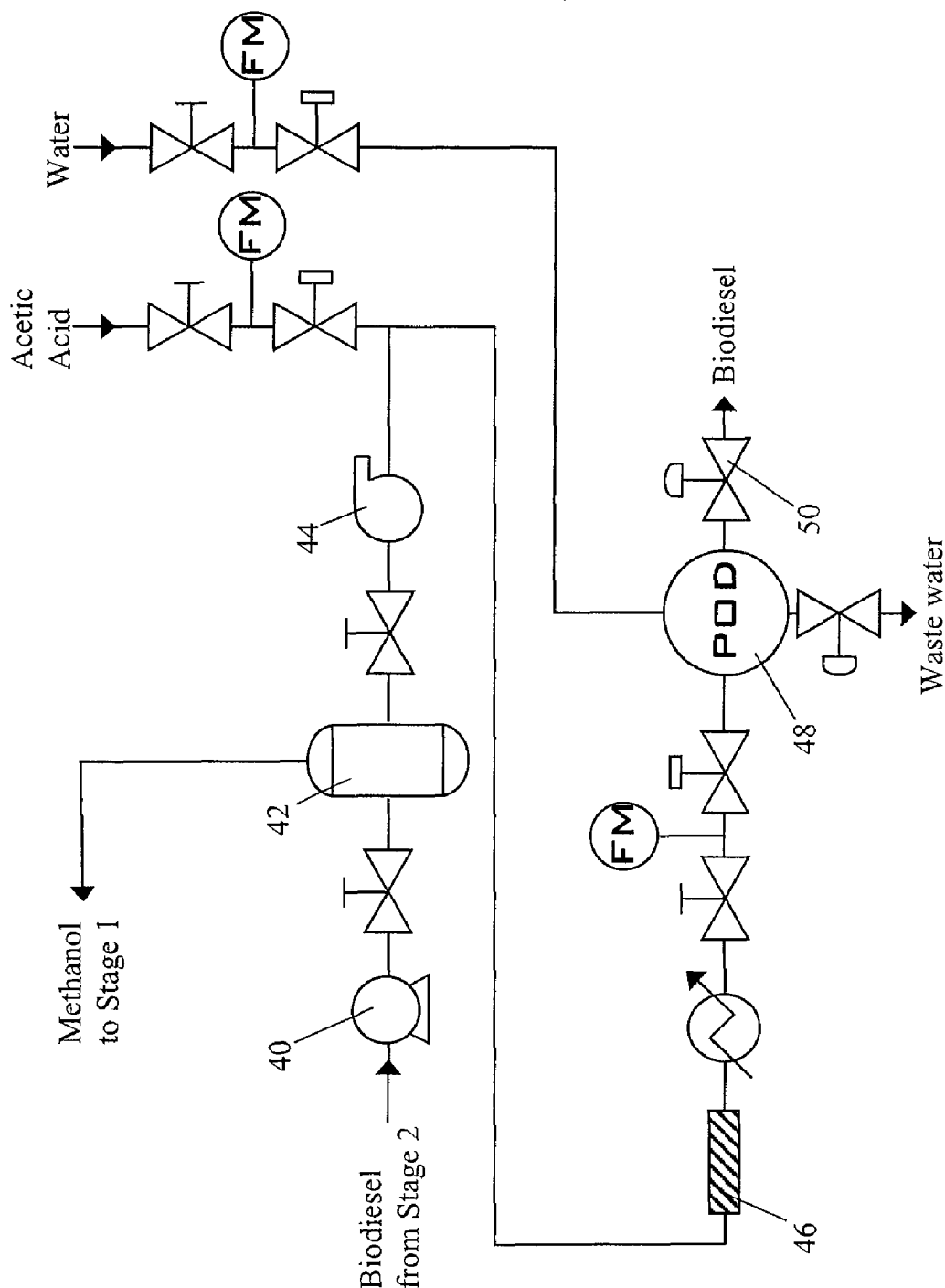
FIG. 1C is a process flow diagram showing a wash stage of the biodiesel production process of FIG. 1A and continuing from FIG. 1B.

A biodiesel production method and apparatus for producing biodiesel, i.e., lower alkyl esters of higher fatty acids, from an oil phase and lower alcohols in a catalytic transesterification process in the presence of an alkaline catalyst are generally shown in FIGS. 1A, 1B, and 1C. According to this method, biodiesel, i.e., lower alkyl esters of higher fatty acids, is produced from an oil phase and lower alcohols in a catalytic transesterification process in the presence of an alkaline catalyst.

In a first transesterification stage shown in FIG. 1A, the inventive method may include providing raw oil comprising oil-phase fatty acid triglycerides in a first feed tank 10 that may be jacketed and temperature controlled at above 25° C. to prevent the oil from solidifying, providing methanol (MEOH) in a second feed tank 12 under a nitrogen blanket, and sodium methylate catalyst (AKA sodium methoxide) in a third feed tank 14, under a nitrogen blanket and temperature controlled to between 10° C. and 30° C. The methanol may be pumped from the second feed tank 12 and heated to at least 65° C. while the sodium methylate in a solution of methanol is pumped from the third feed tank 14 and heated to at least 65° C. and oil is pumped from the first feed tank 10 and heated to at least 65° C. The methanol is combined with the sodium methylate solution before being combined with the oil, the sodium methylate being metered at a rate of between 1.0 and 1.5% (preferably 1.13%) of the weight of the incoming oil, and the methanol being metered at a rate of 150% of the stoichiometric requirement. In other words, oil from the first feed tank 10 is mixed with a solution of methanol (MEOH) from the second feed tank 12 and an alkaline catalyst from the third feed tank 16 comprising sodium methylate (AKA sodium methoxide) at 150% stoichiometric MEOH, such that the catalyst comprises 1.13% by weight of incoming oil flow.

As is also shown in FIG. 1A, the resulting first stage reaction mixture may immediately be subjected to high-intensity mixing and high temperature to begin a rapid transesterification reaction. For example, and as shown in FIG. 1A, the first stage reaction mixture may be pumped first through an inline static mixer 18 and then into a first stage pressure vessel buffer tank 20 that may include an agitator. As it flows through the first stage pressure vessel buffer tank 20 the first stage reaction mixture may be maintained at a temperature above the 65 degree C. boiling point of methanol over a residence period of 5 minutes. However, in other embodiments or implementation of this process, the first stage reaction mixture may be maintained at any suitable temperature within a workable range of 65-250 degrees C., with 250 degrees C. being the upper temperature limit of a POD-type centrifugal separator 22 that may be used in the process as described below. The first stage buffer tank 20 and any other vessels and lines containing methanol may be pressurized by nitrogen as required to prevent boil off that might otherwise occur as a result of the elevated temperature of the first stage reaction mixture.

Glycerin is then separated from a resulting first stage reaction product stream by using a phase separation process that includes continuously pumping the first stage reaction product stream into a "light liquid" inlet 24 of the first stage centrifugal separator shown at 22 in FIG. 1A, i.e., an inlet located close to an outer rim region of the first stage centrifugal separator 22. A glycerin phase of the first stage reaction product stream is then separated from a biodiesel phase of the first stage reaction product stream with the heavier glycerin phase being centrifuged radially outward to the rim region of the first stage centrifugal separator 22. The lighter biodiesel phase is displaced radially inward to an axial region of the first stage centrifugal separator 22.

As shown in FIG. 1A, the first stage centrifugal separator 22 may be of the POD type, which is available from B&P Process Systems of Saginaw Michigan, the assignee of the present invention, and is configured for and typically used in counter-current extraction processes. Where a POD is used as the first-stage centrifugal separator 22, the glycerin and biodiesel phases must pass through arrays of perforations in a series of concentric cylindrical panels separating the axial region from the rim region of the POD. The glycerin and biodiesel phases pass through arrays of perforations in the panels of the series of concentric panels as the glycerin passes to the rim region and the biodiesel phase passes to the axial region of the separator. Passing the reaction product stream through the perforations of a POD imparts shear at the phase separating point and, therefore, additional mixing.

The first stage centrifugal separator 22 then discharges the glycerin phase of the first stage reaction product stream in one stream and discharges the biodiesel phase of the first stage reaction product stream in a second stream. The first stage centrifugal separator 22 may be pressurized to 53-175 psig to allow high temperatures to be maintained without boil off. This pressurization is achieved and maintained using a first stage pump 24 disposed upstream from the first stage centrifugal separator 22 and back-pressure imparted and controlled using a first stage regulating valve 26 disposed downstream from the first stage centrifugal separator 22 as shown in FIG. 1A.

All of the biodiesel phase of the first stage reaction product stream exiting the first stage centrifugal separator 22 may then be passed through a first second stage pump 28 to a second stage of transesterification and glycerin separation shown in FIG. 2A. In the second stage the above steps may be repeated by combining, through high-intensity mixing, and at high temperature and pressure, the biodiesel phase of the first stage reaction product stream with an additional dose of methanol and alkaline catalyst with methanol comprising 25% of the stoichiometric amount based on the starting oil flow rate, and sodium methylate solution comprising 0.15% by weight of the starting oil flow rate. Optionally, the combined streams may flow through a second stage high-shear mixer 30 to further drive reaction kinetics.

The resulting second stage reaction mixture may then be propelled into an agitated and pressurized second stage buffer tank 32 for a residence period of, for example, 20 minutes at controlled temperatures. The resulting second stage reaction product stream may then be passed through a second stage centrifugal separator 34 at high temperature and pressure to remove additional glycerin. As with the first stage centrifugal separator 22, the second stage centrifugal separator 34 may be a POD-type centrifugal separator incorporated and used in the same manner as described with regard to stage one, above.

As in the first transesterification stage, pressurization may be achieved and maintained using a second stage pump 36 disposed upstream from the second stage centrifugal separator 34 and back-pressure imparted and controlled using a second stage regulating valve 38 disposed downstream from the second stage centrifugal separator 34.

All of the separated biodiesel phase (biodiesel product) of the second stage reaction product stream may be passed on to a wash stage as shown in FIG. 3A, propelled by a first wash stage pump 40. The wash stage may include a stripping step in which surplus unreacted methanol is stripped from the biodiesel product by passing the biodiesel product through a vacuum distillation tower 42. The resulting distilled methanol may be passed back to be recycled for use in the first and/or second stage of the process.

At least a portion of any remaining catalyst that did not separate out with the glycerin may then be neutralized by using a second wash stage pump 44 to propel the biodiesel product through an inline static mixer 46 along with an acid such as acetic acid introduced into the biodiesel product downstream from the second wash stage pump 44.

Free glycerin and any remaining traces of methanol and catalyst may then be washed from the biodiesel product using a counter-current extraction process that includes continuously passing the unwashed biodiesel product into a radially outer region of a wash stage POD centrifugal separator 48, heating fresh unrecycled water to 70 degrees C. (65-250 degrees C.), and separating catalyst from the biodiesel product by continuously passing the water in counter flow fashion at a rate of 1-10% (optimally 2-5%) of the incoming biodiesel flow rate into a central axial region of the wash stage POD centrifugal separator 48 such that the water is forced radially outward through the radially-inwardly moving biodiesel product and, while doing so, both the water and the biodiesel product are forced to pass through arrays of perforations in a series of concentric cylindrical panels within the wash stage POD, presenting additional surface area contact between the water and the biodiesel product.

The wash stage POD centrifugal separator 48 may be pressurized to about 22-68 psig to allow high temperatures to be maintained without boil off. As in the first and second transesterification stages, this pressurization may be achieved and maintained using a pump, i.e., the second wash stage pump 44 and a regulating valve 50. More specifically, and as shown in FIG. 3A, the second wash stage pump 44 is disposed upstream from the wash stage centrifugal separator 48 and back-pressure is imparted and controlled using a wash stage regulating valve 50 disposed downstream from the wash stage centrifugal separator 48. The glycerin, methanol, and catalyst may be continuously discharged with the wash water in one stream from the centrifugal separator and resulting washed biodiesel product may be continuously discharged in a second stream at a purity of between 99 and 100%.

Where high intensity mixing and high temperature are employed in both the first and second stages as described above, the speed of the transesterification reactions is dramatically increased so that their duration may be dramatically decreased. Decreased reaction time reduces the number of side reactions and reduces required plant footprint size. The use of a counter-current centrifugal separator allows glycerin, catalyst, and methanol to be washed more quickly and completely from the biodiesel product and minimizes the amount of wash water required. The use of counter-current extraction in the wash stage allows high purity biodiesel to be produced more quickly, using less equipment, and requiring less floor space.

This description, rather than describing limitations of an invention, only illustrates one embodiment of the invention recited in the claims. The language of this description is therefore exclusively descriptive and is non-limiting. Obviously, it's possible to modify this invention from what the description teaches. Within the scope of the claims, one may practice the invention other than as described above.

What is claimed is:

1. A process for producing lower alkyl esters of higher fatty acids from an oil phase and lower alcohols, in a catalytic transesterification process in the presence of an alkaline catalyst, the process including the steps of:
   providing a reaction mixture by mixing oil comprising oil-phase fatty acids, with a solution comprising methanol (MEOH) and an alkaline catalyst comprising sodium methylate to commence a transesterification reaction producing a reaction product stream comprising biodiesel and glycerin phases; and
   accelerating the transesterification reaction of the reaction mixture by subjecting the reaction mixture to a temperature above the boiling point of methanol and pressurizing the reaction mixture sufficiently to prevent boil-off.

2. The method of claim 1 in which the step of accelerating the transesterification reaction includes further accelerating the reaction through high-intensity mixing of the reaction mixture.

3. The method of claim 1 in which the step of accelerating the transesterification reaction includes subjecting the reaction mixture to a temperature in the range of 65-250 degrees C.

4. The method of claim 1 including the additional step of separating the glycerin phase from the biodiesel phase of the reaction product stream by passing the reaction mixture through a centrifugal separator comprising a series of perforated concentric panels separating an axial region from a rim region of the separator, such that the glycerin and biodiesel phases pass through arrays of perforations in the panels of the series of concentric panels as the glycerin passes to the rim region and the biodiesel phase passes to the axial region of the separator.

5. The method of claim 1 in which the step of providing a reaction mixture includes mixing oil comprising oil-phase fatty acids, with a solution comprising methanol (MEOH) and an alkaline catalyst comprising sodium methylate at approximately 150% stoichiometric MEOH.

6. The method of claim 1 in which the step of providing a reaction mixture includes providing sufficient alkaline catalyst to comprise approximately between 1.0 and 1.5% of the weight of the oil.

7. The method of claim 1 in which:
the method includes the additional steps of:
separating the glycerin phase from the biodiesel phase of the reaction product stream;
providing a second stage reaction mixture by mixing the biodiesel phase of the reaction product stream with additional methanol and alkaline catalyst; and
accelerating the transesterification reaction of the second stage reaction mixture by subjecting the second stage reaction mixture to a temperature in the range of 65-250 degrees C. and pressurizing the second stage reaction mixture sufficiently to prevent boil-off.

8. The method of claim 7 in which the step of accelerating the transesterification reaction includes further accelerating the reaction through high-intensity mixing of the second stage reaction mixture.

9. The method of claim 7 in which the step of providing a second stage reaction mixture includes mixing the biodiesel phase with a solution comprising methanol (MEOH) and an alkaline catalyst comprising sodium methylate at approximately 25% stoichiometric MEOH.

10. The method of claim 7 in which the step of providing a second stage reaction mixture includes providing sufficient alkaline catalyst to comprise approximately 0.15% by weight of incoming flow of the biodiesel phase.

11. The method of claim 1 including the additional steps of:
separating the glycerin phase from the biodiesel phase of the reaction product stream; and
stripping surplus unreacted methanol from the biodiesel phase by passing the biodiesel phase through a vacuum distillation tower.

12. The method of claim 11 including the additional steps of:
passing the stripped unreacted methanol into a condensation system to be condensed; and
passing condensed methanol from the condensation system back to be recycled for use in the step of providing a reaction mixture.

13. The method of claim 1 including the additional steps of:
separating the glycerin phase from the biodiesel phase of the reaction product stream by passing the reaction mixture through a centrifugal separator; and
neutralizing any remaining catalyst by passing the biodiesel product through an inline static mixer and mixing the biodiesel product with an acid.

14. The method of claim 1 including the additional steps of separating the glycerin phase from the biodiesel phase of the reaction product stream; and
washing a resulting biodiesel product using counter-current extraction.

15. The method of claim 14 in which the step of washing the biodiesel product includes continuously passing biodiesel product into a radially outer rim region of a counter-current centrifugal separator and continuously passing water in counter-flow fashion into a central axial region of the centrifugal separator such that the water is forced radially outward through the biodiesel product as the biodiesel product passes radially inward toward the central axial region.

16. The method of claim 15 in which the counter-current centrifugal separator includes a series of perforated concentric cylindrical panels separating an axial region from a rim region of the separator, such that the water and the biodiesel product are passed in counterflow fashion through arrays of perforations in the panels of the series of concentric panels as the water passes to the rim region and the biodiesel product passes to the axial region of the separator.

17. The method of claim 1 including the additional steps of:
separating the glycerin phase from the biodiesel phase of the reaction product stream; and
washing the biodiesel phase in a single-step water wash process at a 1-10% ratio of water to unwashed biodiesel phase.

18. The method of claim 17 in which the washing step includes washing the biodiesel phase in a single-step water wash process at a 2-5% ratio of water to unwashed biodiesel phase.

19. The method of claim 1 including the additional steps of:
separating a first stage glycerin phase from a first stage biodiesel phase of a resulting first stage reaction product stream by passing the first stage reaction mixture through a centrifugal separator comprising a series of perforated concentric panels separating an axial region from a rim region of the separator, such that the first stage glycerin and biodiesel phases pass through arrays of perforations in the panels of the series of concentric panels as the first stage glycerin phase passes to the rim region and the first stage biodiesel phase passes to the axial region of the separator;
providing a second stage reaction mixture by mixing the first stage biodiesel phase with additional methanol and alkaline catalyst comprising sodium methylate;
accelerating the transesterification reaction of the second stage reaction mixture by subjecting the second stage reaction mixture to high-intensity mixing at a temperature in the range of 65-250 degrees C. and pressurizing the second stage reaction mixture sufficiently to prevent boil-off;
separating a second stage glycerin phase from a second stage biodiesel phase of a resulting second stage reaction product stream by passing the second stage reaction mixture through a centrifugal separator comprising a series of perforated concentric panels separating an axial region from a rim region of the separator, such that the second stage glycerin and biodiesel phases pass through arrays of perforations in the panels of the series of concentric panels as the second stage glycerin phase passes to the rim region and the second stage biodiesel phase passes to the axial region of the separator;
stripping surplus unreacted second stage methanol from the second stage biodiesel phase by passing the second stage biodiesel phase through a vacuum distillation tower;
producing unwashed biodiesel product by, following the methanol stripping step, neutralizing at least a portion of any remaining catalyst by passing the second stage biodiesel phase through an inline static mixer and mixing the second stage biodiesel phase with an acid; and
producing a washed biodiesel product by continuously passing the unwashed biodiesel product into a radially outer rim region of a counter-current centrifugal separator comprising a series of perforated concentric cylindrical panels separating a central axial region from the outer rim region of the separator, and continuously passing water in counter-flow fashion into the central axial region of the centrifugal separator such that the water moves radially outward through arrays of perforations in the panels of the series of concentric panels as the biodiesel product moves radially inward through the arrays of perforations toward the central axial region.

20. A process for producing lower alkyl esters of higher fatty acids from an oil phase and lower alcohols, in a catalytic transesterification process in the presence of an alkaline catalyst, the process including the steps of:
providing a first stage reaction mixture by mixing oil comprising oil-phase fatty acids, with a solution comprising methanol (MEOH) and an alkaline catalyst comprising sodium methylate; and
separating a first stage glycerin phase from a first stage biodiesel phase of a resulting first stage reaction product stream by passing the first stage reaction mixture through a first stage centrifugal separator comprising a series of perforated concentric panels separating an axial region from a rim region of the separator, such that the first stage glycerin and biodiesel phases pass through arrays of perforations in the panels of the series of concentric panels as the glycerin passes to the rim region and the first stage biodiesel phase passes to the axial region of the separator.

21. The method of claim 20 in which, following the step of providing a first stage reaction mixture and before the step of separating a first stage glycerin phase, the transesterification reaction of the reaction mixture is accelerated by subjecting the first stage reaction mixture to a temperature above the boiling point of methanol and pressurizing the reaction mixture sufficiently to prevent boil-off.

22. The method of claim 21 in which the step of accelerating the transesterification reaction includes further accelerating the reaction through high-intensity mixing of the first stage reaction mixture.

23. The method of claim 21 in which the step of accelerating the transesterification reaction includes subjecting the first stage reaction mixture to a temperature in the range of 65-250 degrees C.

24. The method of claim 20 in which the step of providing a first stage reaction mixture includes mixing oil comprising oil-phase fatty acids, with a solution comprising methanol (MEOH) and an alkaline catalyst comprising sodium methylate at approximately 150% stoichiometric MEOH.

25. The method of claim 20 in which the step of providing a first stage reaction mixture includes providing sufficient alkaline catalyst to comprise approximately between 1.0 and 1.5% of the weight of the oil.

26. The method of claim 20 in which, following the step of separating a first stage glycerin phase, the method includes the additional steps of:
providing a second stage reaction mixture by mixing the first stage biodiesel phase of a first stage reaction product stream with additional methanol and alkaline catalyst; and
separating a second stage glycerin phase of a resulting second stage reaction product stream from a second stage biodiesel phase of the second stage reaction product stream by passing the second stage reaction mixture through a second stage centrifugal separator comprising a series of perforated concentric panels separating an axial region from a rim region of the separator, such that the second stage glycerin and biodiesel phases pass through arrays of perforations in the panels of the series of concentric panels as the glycerin passes to the rim region and the second stage biodiesel phase passes to the axial region of the separator.

27. The method of claim 26 in which the step of providing a second stage reaction mixture includes mixing the first stage biodiesel phase with a solution comprising methanol (MEOH) and an alkaline catalyst comprising sodium methylate at approximately 25% stoichiometric MEOH.

28. The method of claim 26 in which the step of providing a second stage reaction mixture includes providing sufficient alkaline catalyst to comprise approximately 0.15% by weight of the incoming first stage biodiesel phase.

29. The method of claim 26 in which, following the step of providing a second stage reaction mixture, the method includes accelerating the transesterification reaction of the second stage reaction mixture by subjecting the second stage reaction mixture to a temperature in the range of 65-250 degrees C. and pressurizing the second stage reaction mixture sufficiently to prevent boil-off.

30. The method of claim 29 in which the step of accelerating the transesterification reaction of the second stage reaction mixture includes further accelerating the reaction through high-intensity mixing of the second stage reaction mixture.

31. The method of claim 26 including the additional step of stripping surplus unreacted second stage methanol from the second stage biodiesel phase by passing the second stage biodiesel phase through a vacuum distillation tower.

32. The method of claim 31 including the additional steps of:
passing the stripped unreacted second stage methanol into a condensation system to be condensed; and
passing condensed second stage methanol from the condensation system back to be recycled for use in the step of providing a reaction mixture.

33. The method of claim 31 in which, following the step of stripping surplus unreacted second stage methanol, any remaining catalyst is neutralized by passing the second stage biodiesel phase through an inline static mixer and mixing the second stage biodiesel phase with an acid.

34. The method of claim 26 including the additional step of washing the second stage biodiesel product using counter-current extraction.

35. The method of claim 34 in which the step of washing the second stage biodiesel phase includes continuously passing second stage biodiesel phase into a radially outer rim region of a counter-current centrifugal separator and continuously passing water in counter-flow fashion into a central axial region of the centrifugal separator such that the water is forced radially outward through the second stage biodiesel phase as the second stage biodiesel phase passes radially inward toward the central axial region.

36. The method of claim 35 in which the counterflow centrifugal separator includes a series of perforated concentric cylindrical panels separating an axial region from a rim region of the separator, such that the water and the second stage biodiesel phase are passed in counterflow fashion through arrays of perforations in the panels of the series of concentric panels as the water passes to the rim region and the second stage biodiesel phase passes to the axial region of the separator.

37. The method of claim 26 including the additional step of washing the second stage biodiesel phase in a single-step water wash process at a 1-10% ratio of water to unwashed second stage biodiesel phase.

38. The method of claim 26 including the additional step of washing the second stage biodiesel phase in a single-step water wash process at a 2-5% ratio of water to unwashed second stage biodiesel phase.

39. The method of claim 20 including the additional steps of:
- accelerating the transesterification reaction of the first stage reaction mixture by subjecting the first stage reaction mixture to high-intensity mixing at a temperature in the range of 65-250 degrees C. and pressurizing the reaction mixture sufficiently to prevent boil-off;
- providing a second stage reaction mixture by mixing the first stage biodiesel phase with additional methanol and alkaline catalyst comprising sodium methylate;
- accelerating the transesterification reaction of the second stage reaction mixture by subjecting the second stage reaction mixture to high-intensity mixing at a temperature in the range of 65-250 degrees C. and pressurizing the second stage reaction mixture sufficiently to prevent boil-off;
- separating a second stage glycerin phase from a second stage biodiesel phase of a resulting second stage reaction product stream by passing the second stage reaction mixture through a centrifugal separator comprising a series of perforated concentric panels separating an axial region from a rim region of the separator, such that the second stage glycerin and biodiesel phases pass through arrays of perforations in the panels of the series of concentric panels as the second stage glycerin phase passes to the rim region and the second stage biodiesel phase passes to the axial region of the separator;
- stripping surplus unreacted second stage methanol from the second stage biodiesel phase by passing the second stage biodiesel phase through a vacuum distillation tower;
- producing unwashed biodiesel product by, following the methanol stripping step, neutralizing at least a portion of any remaining catalyst by passing the second stage biodiesel phase through an inline static mixer and mixing the second stage biodiesel phase with an acid; and
- producing a washed biodiesel product by continuously passing the unwashed biodiesel product into a radially outer rim region of a counter-current centrifugal separator comprising a series of perforated concentric cylindrical panels separating a central axial region from the outer rim region of the separator, and continuously passing water in counter-flow fashion into the central axial region of the centrifugal separator such that the water moves radially outward through arrays of perforations in the panels of the series of concentric panels as the biodiesel product moves radially inward through the arrays of perforations toward the central axial region.

40. A process for producing lower alkyl esters of higher fatty acids from an oil phase and lower alcohols, in a catalytic transesterification process in the presence of an alkaline catalyst, the process including the steps of:
- providing a reaction mixture by mixing oil comprising oil-phase fatty acids, with a solution comprising methanol (MEOH) and an alkaline catalyst comprising sodium methylate;
- separating a glycerin phase from a biodiesel phase of a resulting reaction product stream; and
- washing the biodiesel phase using counter-current extraction.

41. The method of claim 40 in which the step of washing the biodiesel phase includes continuously passing the biodiesel phase into a radially outer rim region of a counter-current centrifugal separator and continuously passing water in counter-flow fashion into a central axial region of the centrifugal separator such that the water is forced radially outward through the biodiesel phase as the biodiesel phase passes radially inward toward the central axial region.

42. The method of claim 41 in which the counterflow centrifugal separator includes a series of perforated concentric cylindrical panels separating an axial region from a rim region of the separator, such that the water and the biodiesel phase are passed in counterflow fashion through arrays of perforations in the panels of the series of concentric panels as the water passes to the rim region and the biodiesel phase passes to the axial region of the separator.

43. The method of claim 40 in which the step of providing a reaction mixture includes mixing oil comprising oil-phase fatty acids, with a solution comprising methanol (MEOH) and an alkaline catalyst comprising sodium methylate at approximately 150% stoichiometric MEOH.

44. The method of claim 40 in which the step of providing a reaction mixture includes providing sufficient alkaline catalyst to comprise approximately between 1.0 and 1.5% of the weight of the oil.

45. The method of claim 40 in which, after the step of separating a glycerin phase from a biodiesel phase and before the step of washing the biodiesel phase, including the additional steps of:
- providing a second stage reaction mixture by mixing the biodiesel phase of the reaction product stream with additional methanol and alkaline catalyst; and
- separating a glycerin phase from a biodiesel phase of the second stage reaction mixture.

46. The method of claim 45 in which, following the step of separating a glycerin phase from a biodiesel phase of the second stage reaction mixture and before the step of washing the biodiesel phase, an additional step is included in which surplus unreacted methanol is stripped from the biodiesel phase by passing the biodiesel phase through a vacuum distillation tower.

47. The method of claim 46 including the additional steps of:
- passing the stripped unreacted methanol into a condensation system to be condensed; and
- passing condensed methanol from the condensation system back to be recycled for use in the step of providing a reaction mixture.

48. The method of claim 46 in which, following the step of stripping surplus unreacted methanol, any remaining catalyst is neutralized by passing the biodiesel phase through an inline static mixer and mixing the biodiesel phase with an acid.

49. The method of claim 46 in which the step of washing the biodiesel phase includes a single-step water wash process at a 1-10% ratio of water to unwashed biodiesel.

50. The method of claim 49 in which the step of washing the biodiesel phase includes a single-step water wash process at a 2-5% ratio of water to unwashed biodiesel.

51. The method of claim 45 in which the step of providing a second stage reaction mixture includes mixing the first stage biodiesel phase with a solution comprising methanol (MEOH) and an alkaline catalyst comprising sodium methylate at approximately 25% stoichiometric MEOH.

52. The method of claim 45 in which the step of providing a second stage reaction mixture includes providing sufficient alkaline catalyst to comprise approximately 0.15% by weight of incoming biodiesel phase.

53. The method of claim 40 in which:
- the step of separating a glycerin phase from a biodiesel phase includes passing the reaction mixture through a centrifugal separator comprising a series of perforated concentric panels separating an axial region from a rim region of the separator, such that the glycerin and biodiesel phases pass through arrays of perforations in the panels of the series of concentric panels as the glycerin phase passes to the rim region and the biodiesel phase passes to the axial region of the separator;

the transesterification reaction of the reaction mixture is accelerated by subjecting the reaction mixture to high-intensity mixing at a temperature in the range of 65-250 degrees C. and pressurizing the reaction mixture sufficiently to prevent boil-off;

a second stage reaction mixture is provided by mixing the biodiesel phase with additional methanol and alkaline catalyst comprising sodium methylate;

the transesterification reaction of the second stage reaction mixture is accelerated by subjecting the second stage reaction mixture to high-intensity mixing at a temperature in the range of 65-250 degrees C. and pressurizing the second stage reaction mixture sufficiently to prevent boil-off;

a second stage glycerin phase is separated from a second stage biodiesel phase of a resulting second stage reaction product stream by passing the second stage reaction mixture through a centrifugal separator comprising a series of perforated concentric panels separating an axial region from a rim region of the separator, such that the second stage glycerin and biodiesel phases pass through arrays of perforations in the panels of the series of concentric panels as the second stage glycerin phase passes to the rim region and the second stage biodiesel phase passes to the axial region of the separator;

surplus unreacted second stage methanol is stripped from the second stage biodiesel phase by passing the second stage biodiesel phase through a vacuum distillation tower;

unwashed biodiesel product is produced by, following the methanol stripping step, neutralizing at least a portion of any remaining catalyst by passing the second stage biodiesel phase through an inline static mixer and mixing the second stage biodiesel phase with an acid; and the step of washing the biodiesel phase includes producing a washed biodiesel product by continuously passing the unwashed biodiesel product into a radially outer rim region of a counter-current centrifugal separator comprising a series of perforated concentric cylindrical panels separating a central axial region from the outer rim region of the separator, and continuously passing water in counter-flow fashion into the central axial region of the centrifugal separator such that the water moves radially outward through arrays of perforations in the panels of the series of concentric panels as the biodiesel product moves radially inward through the arrays of perforations toward the central axial region.

* * * * *